US008213571B2

(12) United States Patent
Toh et al.

(10) Patent No.: US 8,213,571 B2
(45) Date of Patent: Jul. 3, 2012

(54) SMALL DIAMETER X-RAY TUBE (75) Inventors: Chin H. Toh, Orange, CA (US); Maurice Peter Bianchi, Palos Verdes Estates, CA (US)

(73) Assignee: The Boeing Company, Chicago, IL (US)

(*) Notice: Subject to any disclaimer, the term of this patent is extended or adjusted under 35 U.S.C. 154(b) by 186 days.

(21) Appl. No.: 12/749,409

(22) Filed: Mar. 29, 2010

(65) Prior Publication Data

US 2011/0235778 A1 Sep. 29, 2011

(51) Int. Cl.
*G01N 23/04* (2006.01)
(52) U.S. Cl. .......................................... 378/57; 378/197
(58) Field of Classification Search ........................ None
See application file for complete search history.

(56) References Cited

U.S. PATENT DOCUMENTS

| | | | |
|---|---|---|---|
| 2,497,543 | A | 2/1950 | Frevel |
| 4,143,275 | A | 3/1979 | Malozzi |
| 5,101,422 | A | 3/1992 | Thiel et al. |
| 5,600,303 | A | 2/1997 | Husseiny et al. |
| 5,692,029 | A | 11/1997 | Husseiny et al. |
| 6,882,703 | B2 | 4/2005 | Price et al. |
| 7,463,714 | B2 | 12/2008 | Edwards et al. |
| 7,508,910 | B2 | 3/2009 | Safai et al. |
| 7,529,343 | B2 | 5/2009 | Safai et al. |
| 7,623,626 | B2 | 11/2009 | Safai et al. |
| 7,649,976 | B2 | 1/2010 | Georgeson et al. |
| 2004/0174949 | A1* | 9/2004 | Yamashita et al. .............. 378/65 |
| 2006/0133575 | A1 | 6/2006 | Gutman et al. |
| 2009/0128557 | A1 | 5/2009 | Finlayson et al. |

OTHER PUBLICATIONS

Hardin, "X-Ray Optics Releases New Potential in Mature Technology", OE Reports, SPIE Newsroom, No. 185, May 1999, pp. 1-5.
"The Basics of Fiber Optic Cable, A Tutorial", retrieved Mar. 9, 2010 from http://www.arcelect.com/fibercable.htm, 12 pgs.
Wikipedia, "Collimator", retrieved Mar. 9, 2010 at http://en.wikipedia.org/wiki/Collimator, 3 pgs.
Wikipedia, "Refractive Index", retrieved Mar. 9, 2010 from http://en.widipedia.org/wiki/Refractive_index, 8 pgs.
International Search Report mailed Jun. 10, 2011.
Mroczka, R. et al., Investigations of X-Ray Metallic Capillaries, Journal of Alloys and Compounds, vol. 401, No. 1-2, pp. 108-117, Sep. 2005.

* cited by examiner

*Primary Examiner* — Hoon Song
(74) *Attorney, Agent, or Firm* — Caven & Aghevli LLC (57) ABSTRACT

Methods and systems for X-ray imaging enable inspection of an area of an object that is located separate and apart from a location of an X-ray generator. An X-ray imaging system includes an X-ray generator to generate X-rays. A collimator filters the generated X-rays to consolidate the generated X-rays and move the generated X-rays in a direction parallel to a centerline axis of the collimator. A small diameter tube transmits the directed X-rays and an end retainer emits the transmitted X-rays at an inspection object. A first filter of the collimator may initially filter the generated X-rays that are not parallel to the centerline axis of the collimator by passing the X-rays through a plurality of apertures. A second filter of the collimator may consolidate the generated X-rays and move the generated X-rays in a direction parallel to the centerline axis of the collimator by passing the generated X-rays through a channel.

17 Claims, 7 Drawing Sheets

SMALL DIAMETER X-RAY TUBE

TECHNICAL FIELD

The present disclosure pertains to X-ray imaging, and more specifically, operations of a small diameter X-ray tube.

BACKGROUND

In some situations, various objects such as vehicles, structures, and/or living organisms call for inspection for the presence of foreign object debris (FOD). For example, a piece of hardware may unintentionally be left inside of a vehicle during manufacturing or maintenance; one or more parasites may infest a structure such as a tree or a home; or a piece of surgical equipment may unintentionally be left inside of a patient during an operation.

In some instances, it is important to inspect the object to determine whether there is a presence of FOD. One technique used to inspect objects for the presence of FOD includes disassembling the object to visually search for FOD. Although disassembly provides access to interior elements that are otherwise difficult to access, this technique is not always plausible and often is cumbersome, time consuming, and/or expensive. For example, it is not plausible to disassemble a tree in order to inspect the tree for the presence of parasites such as beetles as this may destroy the tree. Additionally, it may be expensive and time consuming to disassemble a vehicle such as an aircraft to search for various FOD especially if the FOD is a living organism and is moving around the vehicle during the inspection.

SUMMARY

Methods and systems utilizing a small diameter tube to inspect objects are disclosed. In one embodiment, an X-ray imaging system includes an X-ray generator to generate X-rays and a collimator to direct the generated X-rays. A small diameter tube may transmit the directed X-rays and an end retainer may emit the transmitted X-rays at an inspection object. In some embodiments, the collimator may include a first filter to filter out generated X-rays that are not parallel to a centerline axis of the collimator and a second filter to consolidate the generated X-rays and move the generated X-rays in a direction parallel to a centerline axis of the collimator.

In another embodiment, a method of inspecting an object includes generating X-rays, directing the generated X-rays, and transmitting the directed X-rays through a small diameter tube. A first filter may initially filter generated X-rays that have a direction of travel that is not parallel to a centerline axis of the tube by passing the X-rays through a plurality of apertures. A second filter may pass the X-rays through a channel to consolidate the generated X-rays and move the generated X-rays in a direction parallel to the centerline axis of the tube.

In a further embodiment, a vehicle inspection system includes an X-ray generator to generate X-rays. A small diameter tube may transmit the generated X-rays. The small diameter tube may include a collimator to direct the X-rays through the small diameter tube. The small diameter tube may further include an end retainer to emit the transmitted X-rays at the vehicle.

The features, functions, and advantages may be independently achievable in various embodiments of the present disclosure or combinable in yet other embodiments.

BRIEF DESCRIPTION OF THE DRAWINGS

The detailed description is described with reference to the accompanying figures. In the figures, the left-most digit(s) of a reference number identifies the figure in which the reference number first appears. The same reference numbers in different figures indicate similar or identical items.

DETAILED DESCRIPTION

Overview

X-ray imaging may advantageously be used to inspect various objects for the presence of foreign object debris (FOD). Techniques for implementing X-ray imaging systems for detection of FOD are disclosed herein. Some techniques include transmitting the X-rays through a small diameter tube. As discussed herein, the small diameter tube may be any tube that transmits X-rays having a frequency of at least $10^{16}$ Hertz. For instance, the small diameter tube may transmit X-rays ranging between $10^{16}$ and $10^{19}$ Hertz. A first filter of the small diameter tube may initially filter the X-rays by passing the X-rays through a plurality of apertures. A second filter of the small diameter tube may consolidate the X-rays and move the X-rays in a direction of flow parallel to a centerline axis of the tube by passing the X-rays through a channel. As discussed herein, the techniques may be implemented on objects such as vehicles, structures, and/or living organisms, which includes without limitation, aircraft, maritime vessels, spacecraft, motor vehicles, mechanical devices, trees, homes, surgical patients, and other vehicles, structures, and/or living organisms that may be susceptible to FOD.

Illustrative System

Figure 1:
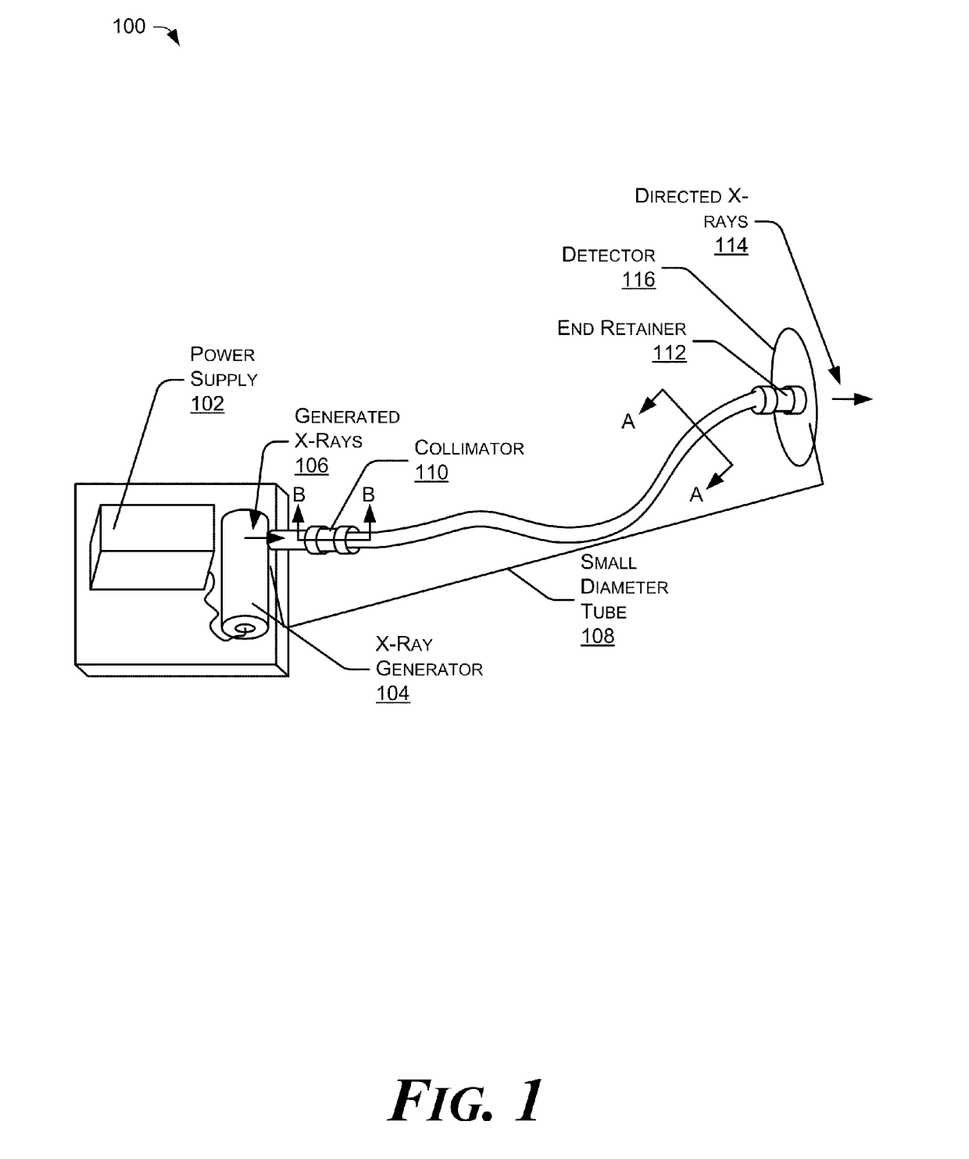
FIG. 1 is schematic diagram of an illustrative X-ray imaging system.

FIG. 1 is a schematic diagram of an illustrative X-ray imaging system 100. In one embodiment, the X-ray imaging system 100 is an X-ray backscatter system. An X-ray backscatter system may be advantageous over transmission X-ray systems since an X-ray backscatter system can transmit and receive the X-ray beam from a same side of the object (i.e., the operator only needs to access one side of the object in order to inspect the object). Another advantage of the X-ray backscatter is that it typically projects less radiation than a transmission X-ray system and so it often requires a smaller exclusion area.

In the illustrative X-ray imaging system 100 of FIG. 1, a power supply 102 may supply power to an X-ray generator 104. The X-ray generator 104 may be operable to generate X-rays 106. The X-ray generator 104 may use any technique well known in the art to generate the X-rays. For instance, the X-ray generator 104 may be a vacuum tube and include a cathode to emit electrons into the vacuum tube. An anode may collect the electrons emitted from the cathode to establish an electrical current through the X-ray generator 104. To generate the X-rays, electrons are boiled off the cathode and collide with the anode under a high energy electric field. If the colliding electrons have sufficient energy, they can knock an electron out of an inner shell of the target metal atoms. X-ray photons with precise energies are emitted when electrons from higher states drop down to fill a vacancy created when the electron is knocked out of the inner shell.

The generated X-rays 106 may pass from the X-ray generator 104 to a small diameter tube 108. The small diameter tube 108 may consist of one or more layers. The small diameter tube 108 may include a collimator 110 proximate the end of the tube that connects to the X-ray generator 104. The collimator 110 may filter and/or direct the generated X-rays 106 in a desired direction of flow. The small diameter tube 108 may additionally include an end retainer 112 to emit directed X-rays 114 at an inspection object. The directed X-rays may contact an inspection area of the inspection object, which may ultimately enable generation of an X-ray image of the inspection area of the inspection object.

In some instances, the end retainer 112 may be designed to fit a specific imaging application. For instance, the end retainer 112 may include a display device to display a real time or near real time X-ray image of the inspection object as the X-ray imaging system 100 images the object. In such instances, the end retainer 112 may be tailored to use the X-ray imaging system 100 as a hand-held detector, for example.

In some embodiments, the X-ray imaging system 100 may include a detector 116 to receive reflected X-rays and/or a radiation shield to absorb reflected X-rays proximate the end retainer 112. The detector 116 and/or the radiation shield may be detachable so that they can be assembled on site and easily stored when not in use.

The small diameter tube 108 advantageously reduces the weight that an operator needs to carry in order to inspect an object. For instance, by separating the heavy power source and/or X-ray generator from the end retainer 112 via the small diameter tube 108, the user of the device need only move the end retainer 112 to a desired inspection location in order to image an object. In addition, since the user need only orient the end retainer 112 at the inspection object, the X-ray imaging system 100 may be used to inspect small or difficult to access areas. For example, the X-ray imaging system 100 may be used to inspect an automobile from inside the vehicle since a user need only move the end retainer 112 and a portion of the small diameter tube 108 inside of the automobile. In some instances, the small diameter tube 108 is of light weight such that a single user may move the end retainer 112 along with one or more portions of the small diameter tube without mechanical assistance or assistance by another user.

Figure 2:
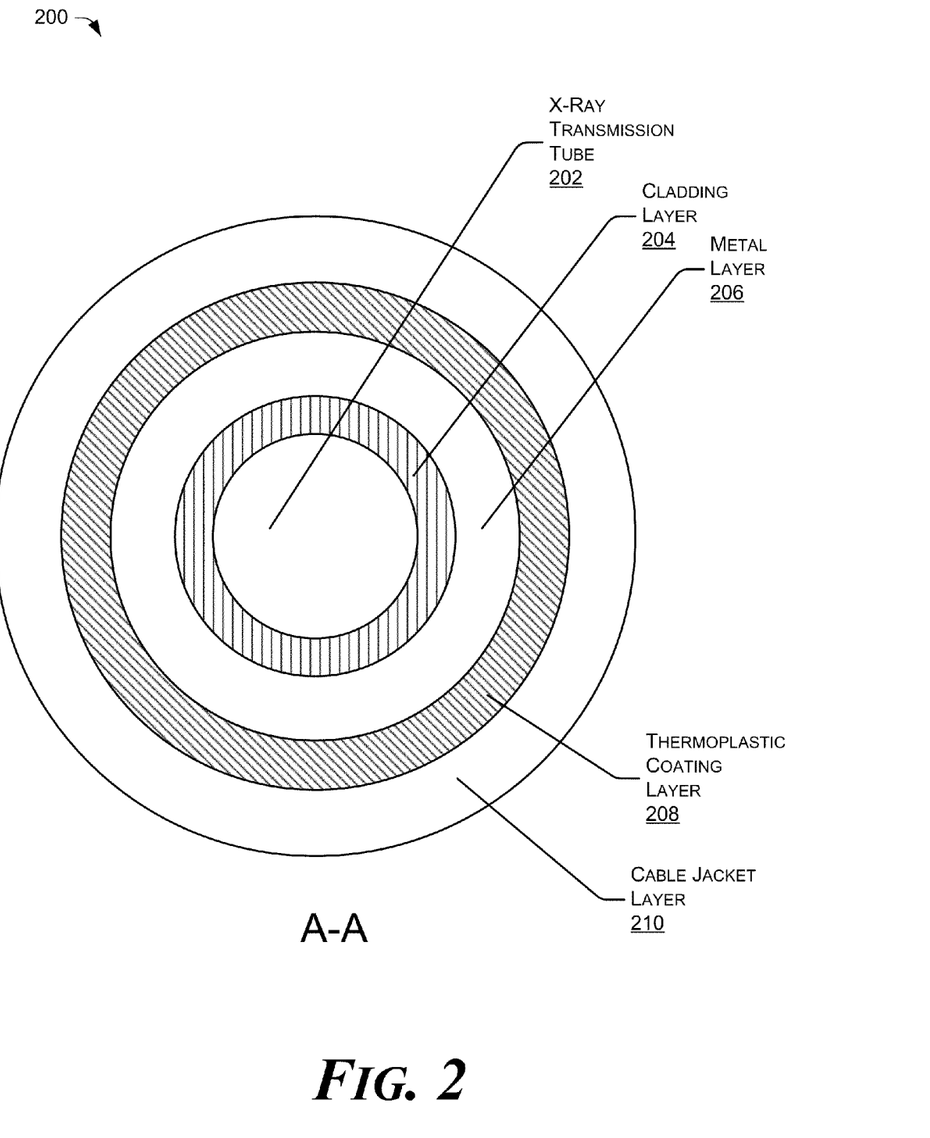
FIG. 2 is a schematic diagram of an illustrative small diameter tube.

FIG. 2 is a schematic diagram of an illustrative small diameter tube element 200. The illustrative small diameter tube element 200 illustrates the components in a cross-section A-A view of the small diameter tube 108 of FIG. 1. An X-ray transmission tube 202 may be located at a core of the small diameter tube 108. The X-ray transmission tube 202 may be formed of any material suitable to transmit X-rays such as (without limitation) copper. A cladding layer 204 may surround the X-ray transmission tube 202. In some instances, the cladding layer 204 is a low refractive index cladding to support a transmission of the X-rays through the small diameter tube 108. A metal layer 206 may surround the cladding layer 204. The metal layer 206 may be formed of a metal suitable to block X-rays, such as lead, tungsten, copper, or aluminum. A thermoplastic coating layer 208 may surround the metal layer 206 to provide added protection to the X-ray transmission tube 202. Finally, a cable jacket layer 210 such as a polyvinyl chloride (PVC) cable jacket may surround the thermoplastic coating layer 208 to provide durability and flexibility to the small diameter tube 108.

In some instances the layering of the illustrative small diameter tube element 200 is similar to typical fiber optics cables used in the telecommunications industry except that the illustrative small diameter tube element includes the X-ray transmission tube 202 at the core and the metal layer 206 to contain the X-rays as they pass through the small diameter tube 108.

Figure 3:
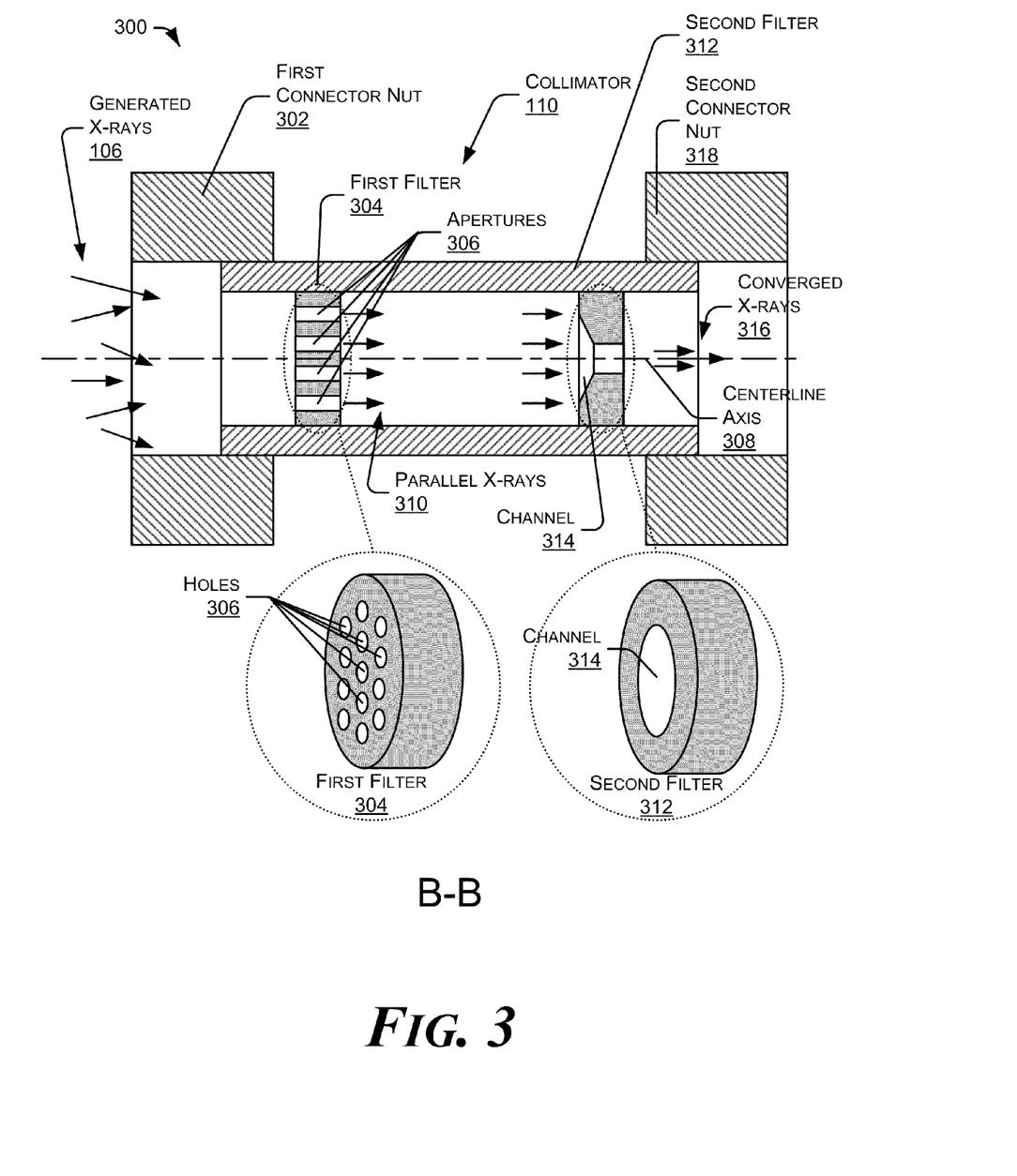
FIG. 3 is a schematic diagram of an illustrative collimator.

FIG. 3 is a schematic diagram of an illustrative collimator element 300 for directing and/or filtering X-rays in a desired direction of flow. The illustrative collimator element 300 illustrates the functions and components in a cross-section B-B view of the collimator 110 of FIG. 1. The X-rays 106 generated by the X-ray generator 104 may enter the collimator 110 through a first connector nut 302. As illustrated in FIG. 3, the generated X-rays 106 may be projected from the X-ray generator 104 at various (random) directions as they enter the first connector nut 302.

The collimator 110 may include a first filter 304 to filter the X-rays. Upon entering the first connector nut 302, the generated X-rays 106 may encounter the first filter 304. The first filter 304 may contain a plurality of apertures 306. The generated X-rays 106 that are in alignment with the apertures 306 and parallel to a centerline axis 308 of the collimator 110 pass through the first filter 304. For instance, parallel X-rays 310 pass through the first filter 304 since they are in alignment with the apertures 306. The generated X-rays 106 that are not in alignment with the apertures 306 will be blocked by the first filter 304 and will not pass through the small diameter tube 108. In some instances, the collimator 110 may share the common centerline axis 308 with the small diameter tube 108.

The collimator 110 may further include a second filter 312 to further direct and/or filter X-rays in a desired direction of flow. The X-rays that pass through the first filter 304 (e.g., parallel X-rays 310) may encounter the second filter 312. The second filter 312 may include a channel 314 to converge the parallel X-rays 310 so that they are consolidated and moving in a direction parallel to the centerline axis 308 of the collimator. The channel 314 may have a conical shape to consolidate and move the parallel X-rays 310 in a direction parallel to the centerline axis 308. For instance, converged X-rays 316 are parallel to and proximate the centerline axis 308 of the collimator 110 as they exit the second filter 312. Upon passing through the second filter 312, the converged X-rays 316 may proceed through the small diameter tube 108. In some instances, the converged X-rays 316 may pass through a second connector nut 318 as they exit the collimator 110 and proceed through the small diameter tube 108.

The various elements of the collimator 110 such as the first connector nut 302, the first filter 304, the second filter 312, and the second connector nut 318 may be formed of a metallic material such as lead tungsten, or aluminum.

Illustrative Process

Figure 4:
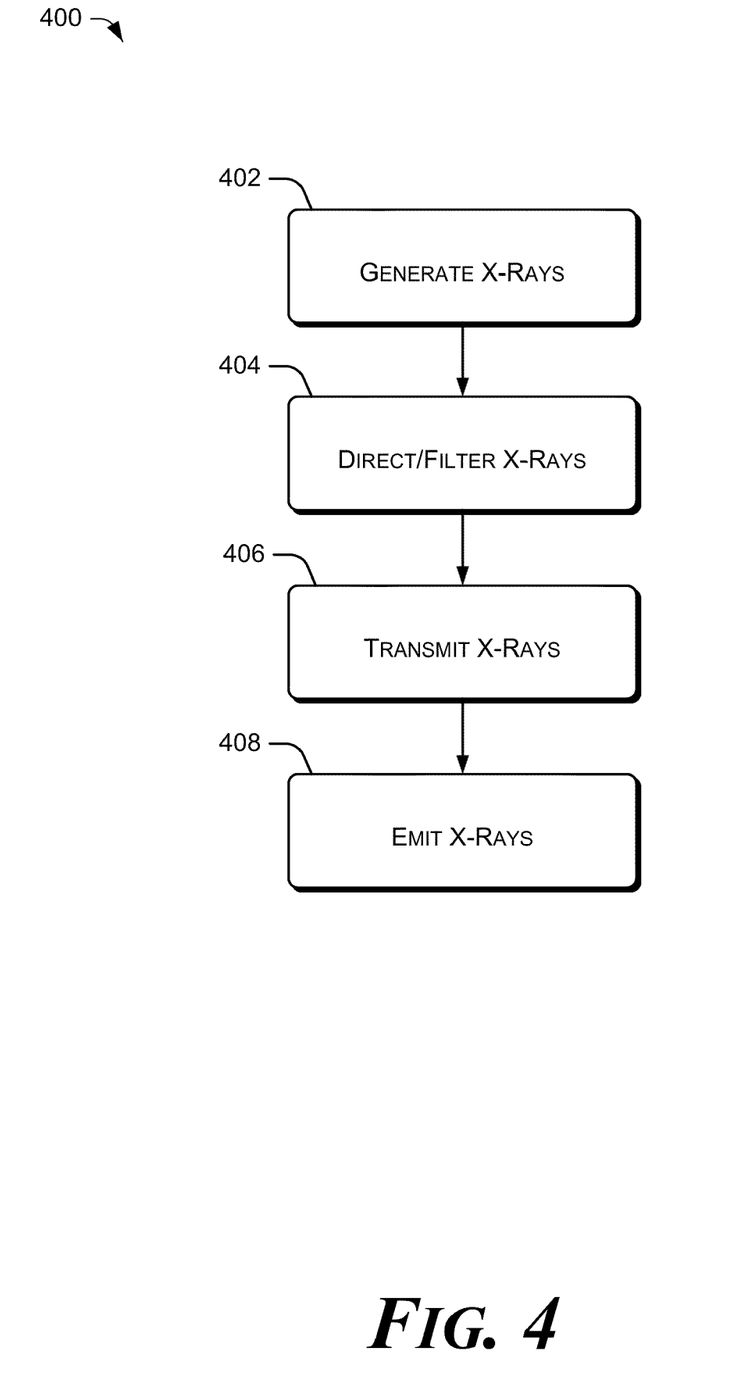
FIG. 4 is a flow diagram of an illustrative process of inspecting an object.

FIG. 4 is a flow diagram of an illustrative process 400 of inspecting an object. The order in which the operations are described is not intended to be construed as a limitation, and any number of the described blocks can be combined in any order and/or in parallel to implement the process. Other processes described throughout this disclosure, in addition to process 400, shall be interpreted accordingly. The process 400 may be performed by the X-ray imaging system 100 of FIG. 1.

At 402, the X-ray generator 104 generates X-rays. Generally, X-rays are generated by bombarding high-speed electrons onto a target to produce the high-energy photons (i.e., high frequency invisible lights).

The generated X-rays pass from the X-ray generator 104 to the collimator 110 where they are directed and/or filtered at 404. The collimator 110 may use one or more filters (e.g., first filter 304 and/or second filter 312) to direct and/or filter the X-rays at 404. In some instances, a circular filter having a plurality of apertures (e.g., first filter 304) filters the X-rays by only allowing X-rays moving in a direction that is parallel to a centerline axis of the collimator 110 and aligned with the apertures to pass through the filter(s). In further instances, a circular filter having a channel (e.g., second filter 312) converges the X-rays so that the X-rays are consolidated near the centerline axis of the collimator 110.

At 406, the X-rays are transmitted through a small diameter tube 108. In some instances the small diameter tube is long enough to enable a user to position and/or orient the tube at an inspection object for imaging. The minimum length of the small diameter tube may vary between 2 and 20 feet depending on the imaging environment. For example, the length of the small diameter tube may be at least 10 feet when used to image an aircraft vehicle. In some embodiments, the length of the small diameter is at least 3 feet in length. In some embodiments, the small diameter tube 108 is of flexible material to enable a user to bend the tube at one or more locations. For instance, the user may bend the tube to position and/or orient the tube at an inspection object for imaging. In addition, the user may bend the tube during imaging to image multiple portions of an imaging object without powering down or relocating the X-ray imaging system.

At 408, the X-rays are emitted from the small diameter tube 108 at an inspection object. The emitted X-rays may be used to generate an X-ray image of the inspection object. For example, the X-rays emitted from the small diameter tube 108 may reflect off the inspection object and are received by a detection unit to generate the X-ray image of the inspection object.

Illustrative Operation

In some instances, the small diameter tube 108 may bend to enable an operator of the X-ray imaging system 100 to move the small diameter tube to a desired imaging position. In situations where the small diameter tube 108 is approximately straight, the X-rays traveling through the small diameter tube will generally move along a centerline axis of the small diameter tube. However, if there are bends in the small diameter tube 108, then the X-rays may deviate from the centerline axis.

Figure 5:
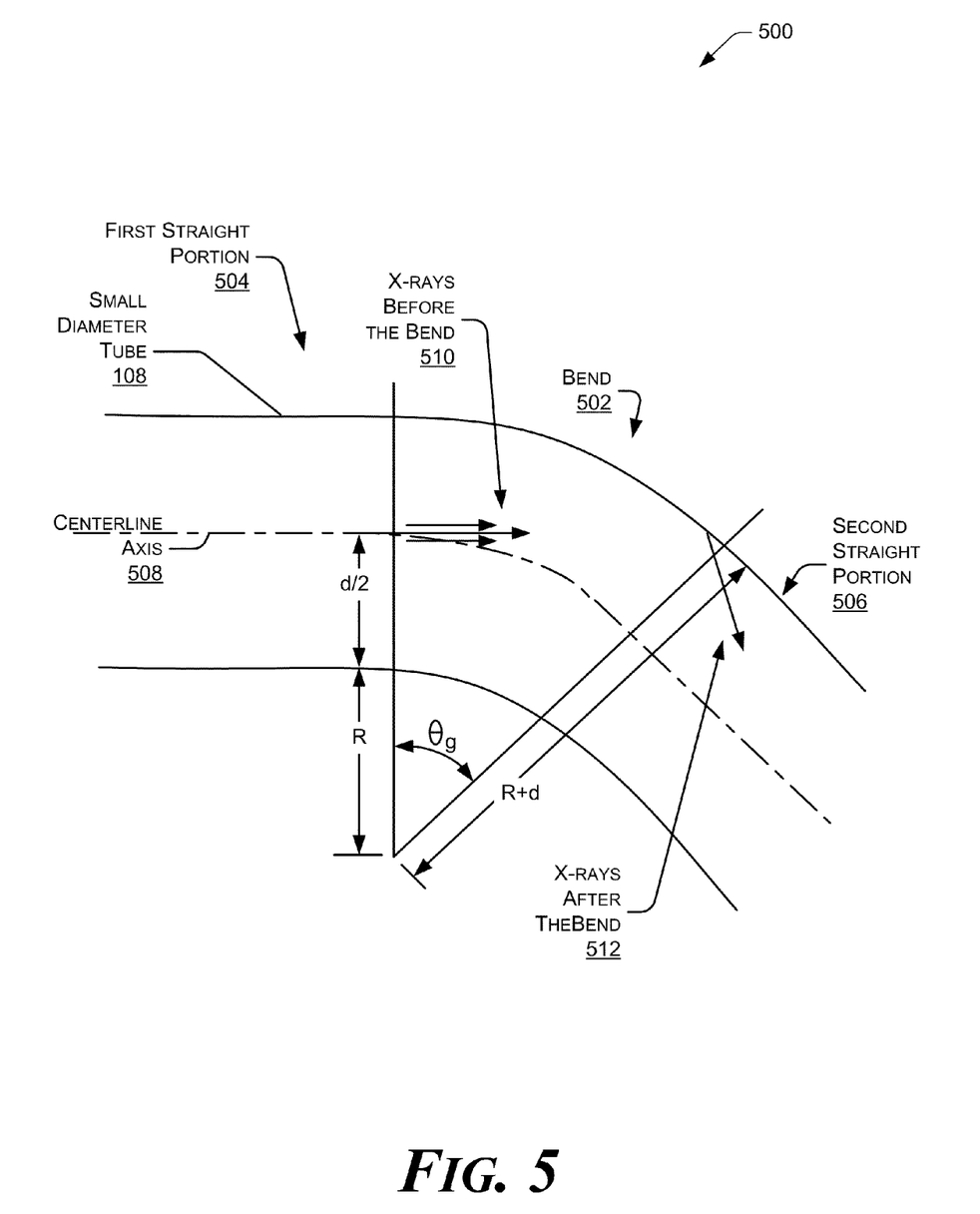
FIG. 5 is a schematic diagram of an illustrative small diameter tube having a bend.

FIG. 5 is an illustrative bent small diameter tube 500 showing X-ray as they are transmitted through a bend 502 of the small diameter tube 108. In some embodiments, the small diameter tube 108 includes a first straight portion 504 and a second straight portion 506 in addition to the bend 502. The small diameter tube 108 has a centerline axis 508 that follows the bend 502. Since X-rays generally belong to the same electromagnetic wave family as visible light, the X-rays traveling through the small diameter tube 108 adhere to principles that have been established for visible light such as the Principle of Total Internal Reflection. Generally, the Principle of Total Internal Reflection of fiber optics states that when an angle of light incidence exceeds a critical value, light cannot escape from the glass fiber but rather bounces back. When applied to the illustrative bent small diameter tube 500 of FIG. 5, the Principle of Total Internal Reflection states that if the bend 502 in the small diameter tube 108 exceeds a critical bend angle, then at least a portion of the X-rays will undesirably be absorbed or blocked by the metal layer 206 rather than traveling through the small diameter tube 108.

In FIG. 5, the bend angle, $\Theta_g$, is defined by the bend radius, R, of the bend 502 in the small diameter tube 108. The larger the bend angle, $\Theta_g$, the more gentle the curvature of the bend; likewise, the smaller the bend angle, $\Theta_g$, the tighter curvature of the bend. When X-rays before the bend 510 encounter the bend 502, a portion of the X-rays 510 may be absorbed/blocked by the metal layer 206 of the small diameter tube. Likewise, a portion of the X-rays my reflect off the metal layer 206 and continue to travel through the small diameter tube 108 as represented in FIG. 5 as X-rays after the bend 512. If the bend angle, $\Theta_g$, reaches or exceeds a critical bend angle, $\Theta_{g,crit}$, then the portion of the X-rays absorbed/blocked by the metal layer 206 may exceed the portion of X-rays that reflect off the metal layer and undesirably reduce a quality of the images generated by the X-ray imaging system. Accordingly, it is important that the bend angles, $\Theta_g$, of the small diameter tube remain less than the critical bend angle, $\Theta_{g,crit}$, during imaging.

The critical bend angle, $\Theta_{g,crit}$, may be defined in Equation 1.

$$\theta_{g,crit} \approx \frac{\omega_p}{\omega} \qquad \text{Equation (1)}$$

In Equation 1, $\omega_p$ denotes an object plasma frequency of the X-ray transmission tube 202 as defined in Equation 2; and $\omega$ denotes the X-ray frequency of X-rays traveling through the X-ray transmission tube 202 (thus through the small diameter tube 108) as defined in Equation 3.

$$(\omega_p)^2 \approx 1.9E^{33}\frac{(z-2)\rho}{A} \qquad \text{Equation (2)}$$

In Equation 2, Z denotes the atomic number of the X-ray transmission tube 202, $\rho$ denotes the mass density of the X-ray transmission tube, and A denotes the atomic weight of the X-ray transmission tube $$\omega = \frac{2\pi C}{\lambda} \qquad \text{Equation (3)}$$

In Equation 3, C denotes the speed of light and $\lambda$ denotes the X-ray wave length of the X-rays traveling through the small diameter tube 108.

Equations 1-3 may be used to calculate the critical bend angle, $\Theta_{g,crit}$, for various X-ray transmission tubes. For instance, Table 1 summarizes the critical bend angle, $\Theta_{g,crit}$, calculated for aluminum, tungsten, and copper without considering the surface finish of the X-ray transmission tube.

TABLE 1

Critical Bend Angle, $\Theta_{g,crit}$, for Various X-ray Transmission Tubes

|  | Aluminum | Tungsten | Copper |
|---|---|---|---|
| Z | 13 | 74 | 29 |
| $\rho$ (g/cm^3) | 2.7 | 19.3 | 8.9 |
| A | 26.98 | 183.84 | 63.55 |
| C (m/s) | 3.00E+08 | 3.00E+08 | 3.00E+08 |
| $\lambda$ (m) | 5.00E-10 | 5.00E-10 | 5.00E-10 |
| $\omega_p^2$ (rad/sec)$^2$ | 2.09E+33 | 1.44E+34 | 7.18E+33 |
| $\omega_p$ (rad/sec) | 4.57E+16 | 1.2E+17 | 8.48E+16 |
| $\omega$ (rad/sec) | 3.77E+18 | 3.77E+18 | 3.77E+18 |
| $\theta_{g,crit}$ (deg) | 0.70 | 1.82 | 1.29 |

Accordingly, Table 1 illustrates that the aluminum, tungsten, and copper all appear to be viable candidate materials for the X-ray transmission tube 202.

The allowable bend radii, R, of the X-ray transmission tube 202 may be defined in Equation 4.

$$R = (\cos(\theta_{g,crit}) - 1/2)\left(\frac{d}{1-\cos(\theta_{g,crit})}\right) \quad \text{Equation (4)}$$

In Equation 4, d denotes the diameter of the X-ray transmission tube 202.

Equations 1-4 may be used to calculate the allowable bend radii, R, for various X-ray transmission tubes. In some instances, X-ray transmission tube 202 determines the allowable bend radius of the small diameter tube 108 using Equations 1-4. Table 2 summarizes the allowable bend radii, R, for aluminum, tungsten, and copper for various tube diameters.

TABLE 2

Bend Radii, R, for Various X-ray Transmission Tubes

| Tube Diameter (inches) | 0.005 | 0.01 | 0.015 | 0.02 | 0.05 |
|---|---|---|---|---|---|
| Aluminum | | | | | |
| $\theta_{g,crit}$ (deg) | 0.70 | 0.70 | 0.70 | 0.70 | 0.70 |
| $\cos(\theta_{g,crit})$ | 0.999925 | 0.999925 | 0.999925 | 0.999925 | 0.999925 |
| Bend Radius (in) | 33.49 | 66.99 | 100.48 | 133.97 | 334.93 |
| Tungsten | | | | | |
| $\theta_{g,crit}$ (deg) | 1.82 | 1.82 | 1.82 | 1.82 | 1.82 |
| $\cos(\theta_{g,crit})$ | 0.999493 | 0.999493 | 0.999493 | 0.999493 | 0.999493 |
| Bend Radius (in) | 4.94 | 9.88 | 14.81 | 19.75 | 49.38 |
| Copper | | | | | |
| $\theta_{g,crit}$ (deg) | 1.29 | 1.29 | 1.29 | 1.29 | 1.29 |
| $\cos(\theta_{g,crit})$ | 0.999747 | 0.999747 | 0.999747 | 0.999747 | 0.999747 |
| Bend Radius (in) | 9.88 | 19.75 | 29.63 | 39.50 | 98.75 |

Table 2 illustrates that a larger diameter tube requires a larger bend radius (that is, more gentle curvature of the bend). Although a diameter of the X-ray transmission tube ranges from 0.005 inches to 0.05 inches in Table 2, the tube may be of any diameter that is less than 6.0 inches. In some instances, the diameter of the tube may less than 2.0 inches. In further instances, the diameter of the tube may be less than 1.0 inches. Alternatively, the diameter of the tube may be less than 0.5 inches such as illustrated in Table 2. With respect to the various materials of the X-ray transmission tube 202, Table 2 illustrates that tungsten can tolerate a tighter bend than copper for any given tube diameter.

Figure 6:
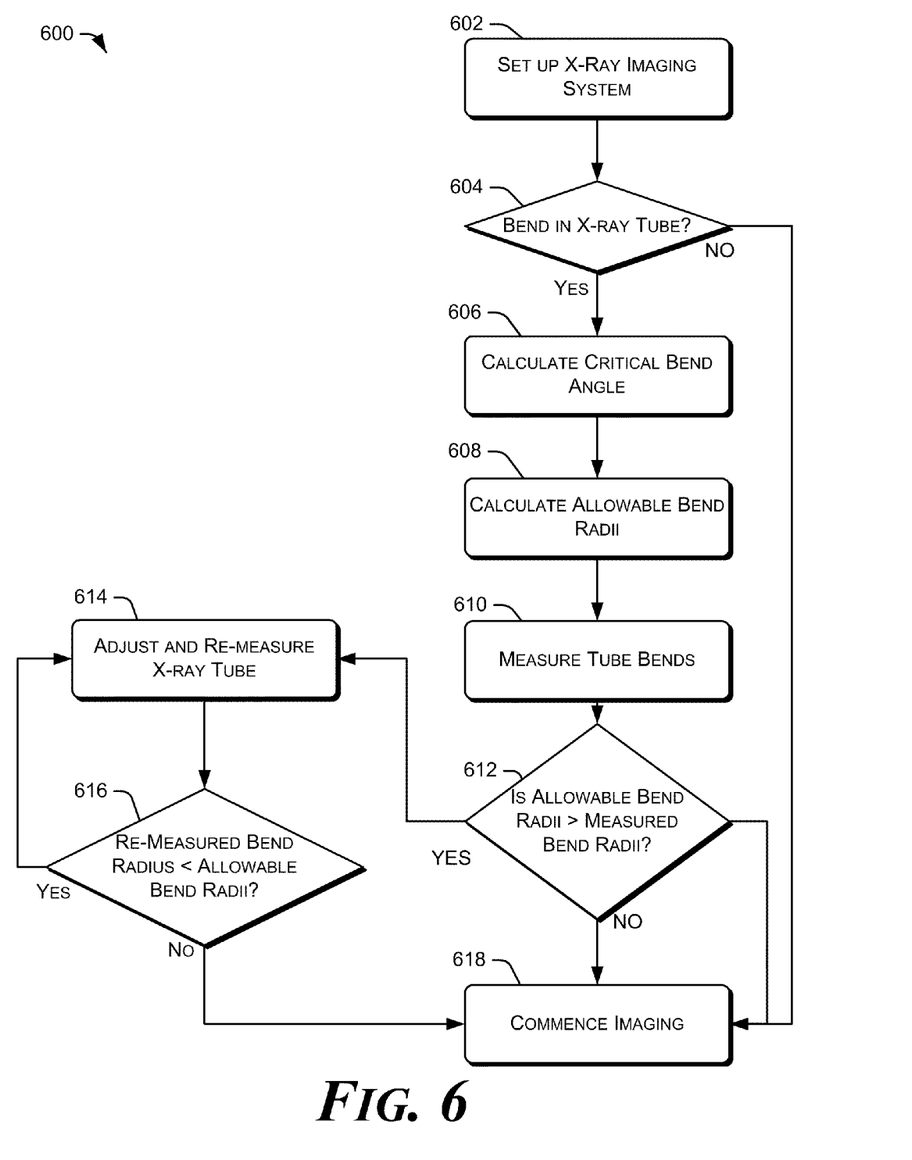
FIG. 6 is a flow diagram of an illustrative process of preparing an X-ray imaging system for imaging.

FIG. 6 is a flow diagram of an illustrative process 600 of preparing an X-ray imaging system for imaging. The process 600 may be performed by the X-ray imaging system 100 of FIG. 1. The order of operations of process 600 is not intended to be construed as a limitation.

At 602, the X-ray imaging system 100 is set up. In some instances, setting up the X-ray imaging system 100 may include connecting the small diameter tube 108 to the X-ray generator 104 and orienting the small diameter tube at an inspection object. In other instances, setting up the X-ray imaging system 100 at 602 may further include connecting the X-ray generator 104 to the power supply 102.

At 604, a determination is made as to whether there are any bends in the small diameter tube 108. If there are no bends in the small diameter tube (i.e., the "No" branch from 604), imaging commences at 618. If there are bends in the small diameter tube (i.e., the "Yes" branch from 604), the critical bend angle, $\Theta_{g,crit}$, is calculated at 606. In some instances, Equations 1 through 3 may be used to calculate the critical bend angle, $\Theta_{g,crit}$, at 606 based on the object plasma frequency of the X-ray transmission tube 202 and the X-ray frequency of X-rays traveling through the small diameter tube.

At 608, the allowable bend radii, R, is calculated. Equation 4 may be used to calculate the allowable bend radii, R, based on the critical bend angle, $\Theta_{g,crit}$, and the diameter of the X-ray transmission tube. In some instances, the X-ray transmission tube determines the critical bend angle and allowable bend radius of the small diameter tube 108.

At 610, the bends of the small diameter tube 108 are measured. Measuring the bends at 610 may include measuring a bend radius of all of the bends in the small diameter tube. At 612, the measured bends of the small diameter tube are compared with the allowable bend radii, R, calculated at 608. If the calculated allowable bend radii, R, is not greater than the measured bend radii (i.e., the "No" branch from 612), imaging commences at 618. If the calculated allowable bend radii, R, is greater than the measured bends (i.e., the "Yes" branch from 612), then the small diameter tube is adjusted at 614. Adjusting the small diameter tube at 614 may include straightening bends of the small diameter tube that are smaller than the allowable bend radii. The bends of the small diameter tube 108 are re-measured at 614.

At 616, the re-measured bends of the small diameter tube are compared with the allowable bend radii, R, calculated at 608. If the re-measured bend radii are more than the calculated allowable bend radii, R, (i.e., the "No" branch from 616), imaging commences at 618. If the re-measured bend radii are less than the calculated allowable bend radii, R, (i.e., the "Yes" branch from 616), then the small diameter tube is adjusted again at 614. In the process 600, the small diameter tube is continually adjusted at 614 until the re-measured bends are more than the calculated allowable bend radii, R, at which point imaging commences at 618. In some embodiments, a user may set-up the X-ray imaging system by laying out the small diameter tube so that the tube is oriented and positioned at the inspection object for imaging. Once the tube is set-up, the user may walk a length of the tube visually inspecting for bends in the tube. For example, if the power source and/or X-ray generator are around a corner from the imaging object, then the small diameter tube will contain at least one bend so that the imaging system may be directed at the inspection object without having to move the power source and the generator. For each bend in the tube, the user may adjust the tube at 614 until the bends in the tube are more than the allowable bend radii. In some embodiments, the X-ray transmission tube 202 enables the small diameter tube 108 to hold its shape when the user adjusts the tube at 614. Alternatively, one or more tube clips may be used to enable the tube to hold its shape during the re-adjustment at 614.

Figure 7:
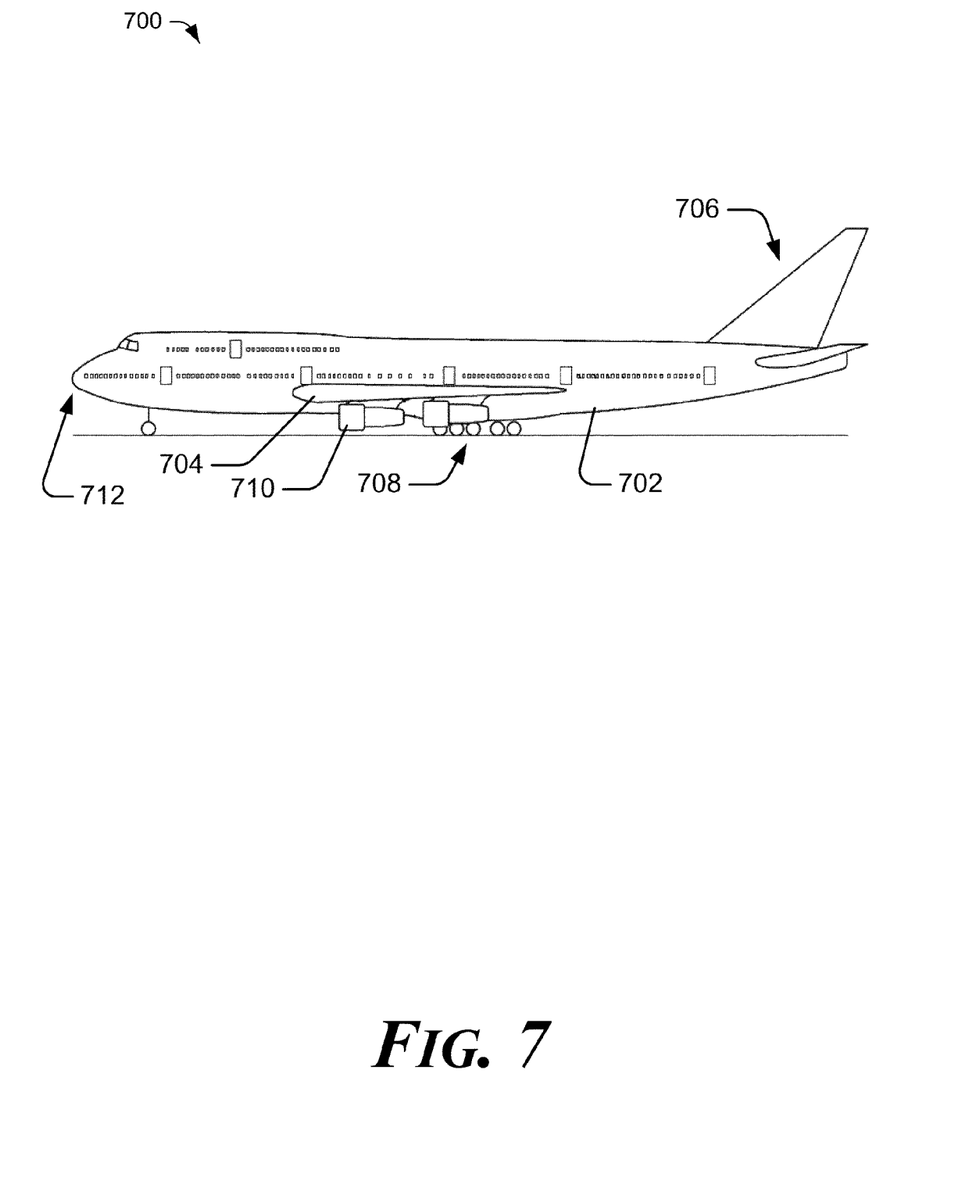
FIG. 7 is a side elevation view of an illustrative aircraft.

FIG. 7 is a side elevational view of an illustrative aircraft 700, which may undergo inspection using the techniques disclosed herein. One may appreciate that the aircraft 700 may include various known and unknown parts, particularly if the aircraft has been in-service for many years, such as an aircraft assembled for large-scale war service (e.g., circa 1945, etc.) Thus, the X-ray imaging system may inspect the aircraft 700 for FOD as disclosed herein.

In this embodiment, the aircraft 700 includes a fuselage 702 including wing assemblies 704, a tail assembly 706, and a landing assembly 708. The aircraft 700 further includes one or more propulsion units 710, a control system 712, and a host of other systems and subsystems that enable proper operation of the aircraft 700. One should appreciate that many parts included in an aircraft may be imaged using the X-ray imaging system techniques disclosed herein.

Although the aircraft 700 shown in FIG. 7 is generally representative of a commercial passenger aircraft; the teachings of the present disclosure may be applied to the inspection of other vehicles, structures, and/or living organisms, that may be susceptible to FOD including fighter aircraft, cargo aircraft, rotary aircraft, other types of manned or unmanned aircraft, ground vehicles, ships, mechanical devices, trees, homes, surgical patients, etc.

CONCLUSION

While embodiments of the disclosure have been illustrated and described, as noted above, many changes can be made without departing from the spirit and scope of the disclosure. Accordingly, the scope of the disclosure is not limited by the disclosure of these embodiments. Instead, the disclosure should be determined entirely by reference to the claims that follow.

What is claimed is:

1. An X-ray imaging system, comprising:
   an X-ray generator to generate X-rays;
   a collimator to direct the X-rays into a direction of flow, a first end of the collimator operatively connected to the X-ray generator;
   a tube element operatively connected to a second end of the collimator opposite the X-ray generator, the tube element to transmit the X-rays from the collimator along the direction of flow towards the inspection object wherein the tube element includes:
   an X-ray transmission tube;
   a cladding layer surrounding the X-ray transmission tube;
   a metal layer surrounding the cladding layer;
   a thermoplastic coating layer surrounding the metal layer; and
   a cable jacket layer surrounding the thermoplastic coating layer; and
   an end retainer coupled to an end of the tube element opposite the X-ray generator, the end retainer to emit the X-rays to the area of inspection.

2. The X-ray imaging system of claim 1, wherein the collimator includes:
   a first filter to filter the generated X-rays; and
   a second filter to transmit the generated X-rays proximate to a centerline axis of the collimator.

3. The X-ray imaging system of claim 2, wherein the first filter and the second filter are formed of a lead, tungsten, or aluminum material.

4. The X-ray imaging system of claim 1, wherein the collimator includes a filter having a plurality of apertures to filter the generated X-rays.

5. The X-ray imaging system of claim 1, wherein the collimator includes a filter having a channel to consolidate the generated X-rays and moving the generated X-rays in a direction parallel to a centerline axis of the collimator.

6. The X-ray imaging system of claim 1, wherein the X-ray generator is separated from the end retainer by a distance of at least 10 feet.

7. The X-ray imaging system of claim 1, wherein the collimator shares a common centerline axis with the small diameter tube.

8. A method of inspecting an area of an object, the method comprising:
   generating X-rays using an X-ray generator;
   filtering the generated X-rays from the X-ray generator using a collimator to block unaligned X-ray beams and to allow aligned X-ray beams to pass through the collimator;
   transmitting the aligned X-rays through a tube element; and
   emitting the aligned X-rays at the object;
   calculating a critical bend radius of the tube element; and
   adjusting the tube element until all bend radii of the tube element are more than the critical bend radius.

9. The method of claim 8, wherein the collimator shares a common centerline axis with the tube element.

10. The method of claim 8, wherein the X-ray generator is part of an X-ray backscatter imaging system.

11. The method of claim 8, wherein the filtering the generated X-rays includes:
    passing the X-rays through a first filter having a plurality of apertures to filter out a portion of the X-rays that are not substantially parallel to a centerline axis of the collimator; and
    passing the X-rays through a second filter having a channel to consolidate and move the X-rays in a direction parallel to the centerline axis of the collimator.

12. The method of claim 11, wherein the first filter and the second filter are formed of either a lead or tungsten material.

13. The method claim 8, wherein the tube element includes:
    an X-ray transmission tube at a core of the tube element;
    a cladding layer surrounding the X-ray transmission tube;
    a metal layer surrounding the cladding layer;
    a thermoplastic coating layer surrounding the metal layer; and
    a cable jacket layer surrounding the thermoplastic coating layer.

14. A vehicle inspection system, comprising:
    an X-ray generator to generate X-rays; and
    a tube element to transmit the X-rays, a first end of the tube element connected to the X-ray generator and a second end of the tube element to emit the X-rays at an object, the tube element including:
    an X-ray transmission tube;
    a cladding layer;
    a metal layer;
    a thermoplastic coating layer; and
    a cable jacket layer;
    a collimator proximate the first end of the tube element, and an end retainer proximate the second end of the small diameter tube element, the collimator and the end retainer separated by a distance.

15. The vehicle inspection system of claim 14, wherein the collimator includes:
   a first filter to filter the generated X-rays via a plurality of apertures; and
   a second filter to converge the generated X-rays via a conical channel.

16. The vehicle inspection system of claim 15, wherein the first filter and the second filter are of either a lead or tungsten material.

17. The vehicle inspection system of claim 14, wherein the collimator shares a common centerline axis with the small diameter tube.

* * * * *